(12) United States Patent
Speitling

(10) Patent No.: US 6,626,912 B2
(45) Date of Patent: Sep. 30, 2003

(54) PROCESS FOR MIXING AND DISPENSING A FLOWABLE SUBSTANCE

(75) Inventor: Andreas Werner Speitling, Kiel (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 09/988,517

(22) Filed: Nov. 20, 2001

(65) Prior Publication Data
US 2002/0087164 A1 Jul. 4, 2002

(30) Foreign Application Priority Data
Nov. 21, 2000 (DE) .......................... 100 57 616

(51) Int. Cl.⁷ .......................... A61F 17/58; B01F 11/00
(52) U.S. Cl. .................. 606/92; 366/209; 366/216; 366/218
(58) Field of Search ............. 606/92, 93; 366/209, 366/216, 218, 116, 110, 210, 211, 212, 219, 237, 239, 240

(56) References Cited

U.S. PATENT DOCUMENTS

| 140,280 A | * | 6/1873 | Keeler ..................... 366/216 |
| 1,421,016 A | | 6/1922 | Leipold |
| 1,489,024 A | * | 4/1924 | Burnett ..................... 366/209 |
| 1,490,214 A | | 4/1924 | Johnson |
| 1,686,135 A | | 10/1928 | Hurdle |
| 2,151,123 A | | 3/1939 | Lavine |
| 3,275,302 A | | 9/1966 | Horton |
| 3,684,136 A | | 8/1972 | Baumann |
| 3,739,947 A | | 6/1973 | Baumann et al. |
| 3,749,371 A | | 7/1973 | Folkenroth et al. |
| 3,756,571 A | | 9/1973 | Winberg |
| 3,828,434 A | | 8/1974 | Mosch |
| 3,831,742 A | | 8/1974 | Gardella et al. |
| 3,917,062 A | | 11/1975 | Winters |
| 4,084,320 A | | 4/1978 | Skeirik |

(List continued on next page.)

FOREIGN PATENT DOCUMENTS

| EP | 0 976 443 | 2/2000 |
| FR | 2 572 677 | 5/1986 |

* cited by examiner

Primary Examiner—Pedro Philogene
Assistant Examiner—D A Bonderer
(74) Attorney, Agent, or Firm—Lerner, David, Littenberg, Krumholz & Mentlik, LLP

(57) ABSTRACT

A process and apparatus for use in mixing and applying a flowable substance that consists of a powdered first component and a liquid second component. The mixing of the two components form a flowable substance, especially a bone cement. The apparatus uses an injection syringe. The first component is placed into the injection syringe after removing the syringe plunger and placing a closing device or cap onto the dispensing end of the syringe. The liquid component is added to the syringe, preferably from a second syringe filled with the liquid component via a hollow needle of the second syringe. The first syringe is closed at the filling with the syringe plunger under the load of sufficient air in the syringe cylinder. The components are mixed by shaking the first syringe. The lid of the first syringe is removed and a hollow needle is placed onto the first syringe and the flowable substance is delivered at a desired site.

19 Claims, 3 Drawing Sheets

U.S. PATENT DOCUMENTS

| | | |
|---|---|---|
| 4,523,855 A | 6/1985 | Walker |
| 4,551,135 A | 11/1985 | Gorman et al. |
| 4,555,183 A | 11/1985 | Thomas |
| 4,648,532 A | 3/1987 | Green |
| 4,652,260 A * | 3/1987 | Fenton et al. .................. 604/67 |
| 4,787,751 A | 11/1988 | Bakels |
| RE33,161 E | 2/1990 | Brown et al. |
| RE33,221 E | 5/1990 | Brown et al. |
| 5,051,482 A * | 9/1991 | Tepic .......................... 525/309 |
| 5,058,770 A | 10/1991 | Herold et al. |
| 5,088,830 A | 2/1992 | Mühlbauer |
| 5,100,241 A | 3/1992 | Chan |
| 5,114,240 A | 5/1992 | Kindt-Larsen et al. |
| 5,167,448 A | 12/1992 | Herold et al. |
| 5,184,893 A | 2/1993 | Steele et al. |
| 5,193,907 A | 3/1993 | Faccioli et al. |
| 5,336,264 A | 8/1994 | Constantz et al. |
| 5,395,167 A | 3/1995 | Murray |
| 5,496,473 A * | 3/1996 | Chow .......................... 210/635 |
| 5,511,879 A | 4/1996 | Fletcher |
| 5,927,851 A | 7/1999 | Carlson |
| 5,971,599 A * | 10/1999 | Bothers ...................... 366/142 |
| 6,083,229 A | 7/2000 | Constantz et al. |
| 6,099,160 A | 8/2000 | Flackett |
| 6,183,515 B1 * | 2/2001 | Barlow et al. ........... 623/16.11 |
| 6,494,611 B2 * | 12/2002 | Edwards et al. ............ 366/209 | ns
PROCESS FOR MIXING AND DISPENSING A FLOWABLE SUBSTANCE

BACKGROUND OF THE INVENTION

The present invention pertains to a process for mixing and applying a flowable substance consisting of two components, and especially bone cement. More particularly the application relates to a two component calcium phosphate bone cement.

As is well known, bone cement is composed of a powdered component and a liquid component that react quickly after mixing. The finished mixture must therefore be processed as quickly as possible. The powdered component, which may be a combination of tetracalcium phosphate and dicalcium phosphate as disclosed in U.S. Reissue Pat. Nos. 33,161 and 33,221, the teachings of which are incorporated herein by reference, is usually supplied in sterile form in a blister pack or a bottle, e.g., with contents of 2 to 25 g. The liquid, e.g., a molar sodium phosphate solution, distilled water or sodium chloride solution is usually present in a sterile, plastic container, usually a disposable syringe having a volume of 10 cc. The two components are usually mixed in a vessel and processed from this vessel, e.g., by means of a syringe or the like. The mixing must be rigorous; on the other hand, the mixing time should not last too long.

SUMMARY OF THE INVENTION

The basic object of the present invention is to specify a process for mixing and applying a flowable substance, and especially bone cement, which can be carried out in an especially simple, effective manner.

This object is accomplished according to the present invention by the following steps:

The powdered component is filled into an injection syringe, which usually has a plunger at one end and a dispensing end, onto which a hollow needle is usually placed. However, the hollow needle is removed and, in its place, a suitable closing means, e.g., a cap is put on. Subsequently, the second, liquid component is filled into the injection syringe, and preferably via, a second syringe, filled with the liquid component via a hollow needled attached thereto. The first syringe is then closed with the syringe plunger under the load of sufficient air in the syringe cylinder. It is also conceivable for the two components to be already located in one syringe, but to be separated from one another by a separating wall. The separating wall is removed or made permeable for the mixing.

The syringe is then shaken rigorously for the purpose of mixing the components. Subsequently, the closing means, i.e. cap, is removed and a hollow needle is placed onto the first syringe, after which the flowable substance is then delivered at a desired site, e.g., at the bone being treated.

The present invention starts from the assumption that the liquid component is packed in a container, for example, in a disposable syringe, and can therefore be relatively simply injected into a syringe that contains the powdered component. This syringe is used as the mixing vessel. It is closed at the ends. It can be moved vigorously, therefore, e.g., even in a mechanical mixing device, so that rigorous mixing can be carried out within the shortest time.

The present invention also pertains to a mixing device, with which a flowable substance, consisting of two components, can be rigorously mixed in the shortest time, e.g., for the formation of a bone cement. Such a mixing device provides an injection syringe with a plunger and a closing device such as a cap on the front end as a mixing vessel for the components filled in. Comparable to the liquid component, the powdered component can likewise be packed in a syringe in sterile form. It is also possible, however, as described above, to fill the powdered component into the cylinder after the removal of the syringe plunger, after which the liquid component is then filled in as well. Subsequently, the plunger is introduced into the cylinder under the load of a sufficient clearance for mixing purposes. The mixing device also has a holder for the detachable holding of the syringe, as well as a mixing system, which imparts on the holder a movement that arises from the superposition of a rotatory and a translatory movement. The mixing system is set into operation by an input shaft, which is driven either manually or by the spindle of a rotating drive motor, e.g., a pneumatically or an electrically driven surgical machine or a separate electric motor. An input transmission is then preferably arranged between the spindle and the input shaft of the mixing system. The input transmission appropriately increases or decreases the speed, before it is transferred to the mixing system. The shaft of the input transmission has a corresponding mount for the drive spindle of the rotating drive motor, which may have a special attachment that can be plugged into the mount.

According to another embodiment of the present invention the holder for the injection syringe of the device according to the present invention is designed as a connecting rod of a connecting-rod drive. For this purpose, the end of the holder may be eccentrically articulated on a rotor, which is coupled with the output shaft of the input transmission, while the other end is mounted in a linearly movable manner.

After the mixing and removal of the syringe, the syringe can be actuated via a dispensing device. According to the present invention, such a dispensing device has a mount for an injection syringe with plunger, such that the dispensing end of the syringe is accessible by hand for the removal of a closing means or cap on the dispensing end and the attachment of a hollow needle. The dispensing device (not shown) which may be similar to a standard caulking gun and has a feed bar, which cooperates with the plunger end of the syringe and is actuated by a hand lever, whose movement is transferred to the feed bar via a transmission. Such dispensing guns have already become known for other purposes, e.g., for pressing sealing material or caulking out of a cartridge, which is inserted into a mount of the gun.

In the present invention, a secure mounting of the syringe in the holder consists of providing a holder having a channel in which the syringe is inserted. Moreover, the channel has, at intervals, transverse grooves, into which the flange of the syringe cylinder can be inserted. In this way, syringes of varying length may be securely mounted on the entire holder. For fixing the syringe to the holder, a web is preferably provided, which crosses the syringe and can be fixed to the holder by means of screws or the like, in order to fix the syringe cylinder in a clamping manner.

BRIEF DESCRIPTION OF THE DRAWINGS

The invention can be performed in various ways and some embodiment will now be described by way of example and with reference to the accompanying drawings in which.

DETAILED DESCRIPTION

Figure 1:
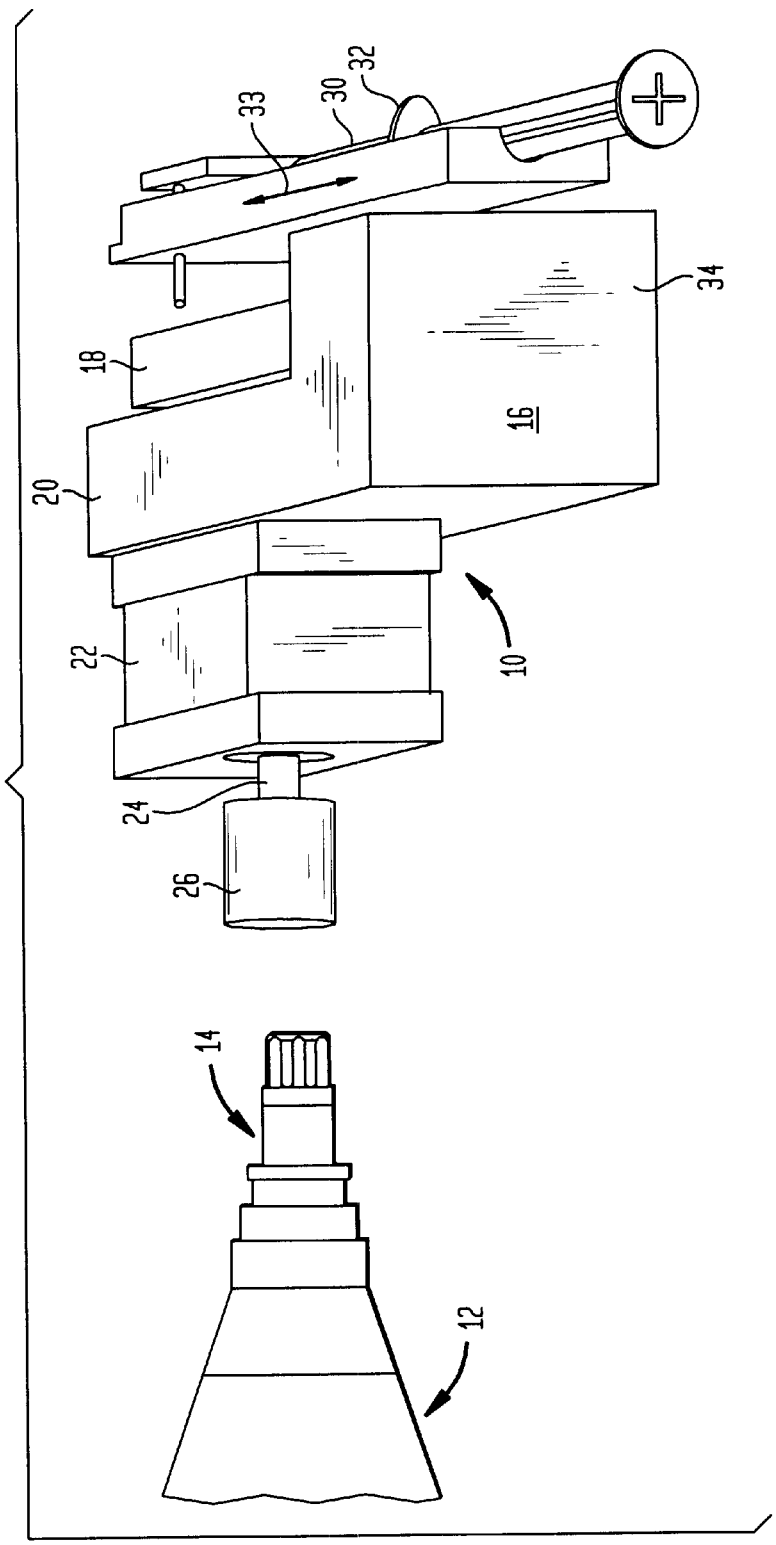
FIG. 1 shows a perspective view of the mixing device according to the present invention.

FIG. 1 schematically shows a mixing device 10, as well as a rotating drive motor 12 shown with a drive spindle 14.

The mixing device 10 has a generally L-shaped base part 16, on one leg of which, on the inside, is rotatably mounted a disk 18. On the opposite side of the leg 20 is located a reducing gear 22, which is in contact with the bearing shaft (not shown) of the disk 18 via its output shaft (not shown). An input shaft 24 of the input transmission 22 has a mount 26 for mounting the drive spindle 14 of the rotating drive motor 12 in a manner adapted to rotate in unison. For coupling purposes, the mount spindle 26 is plugged on drive 14.

An oblong holder 30 for an injection syringe 32 is mounted in a linearly movable manner on the other leg 34 of base part 16 in its longitudinal direction according to the double arrow 33. A pin 60 (shown in FIG. 3) of disk 18 is in rotational connection with the lower side of holder 30. The pin 60 is attached eccentrically to the disk 18. Therefore, a rotation of the disk 18 leads to a superimposed movement from the rotation of the disk 18 and from the forced translatory movement of the holder 30.

Figure 2A:
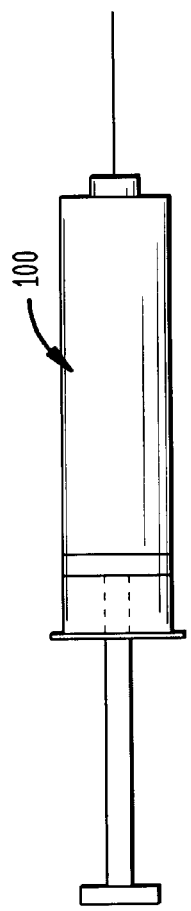
FIG. 2 A is an elevation view of a second syringe containing a liquid component.
FIG. 2B shows a top view of the mixing device with the mounted injection syringe.
Figure 2B:
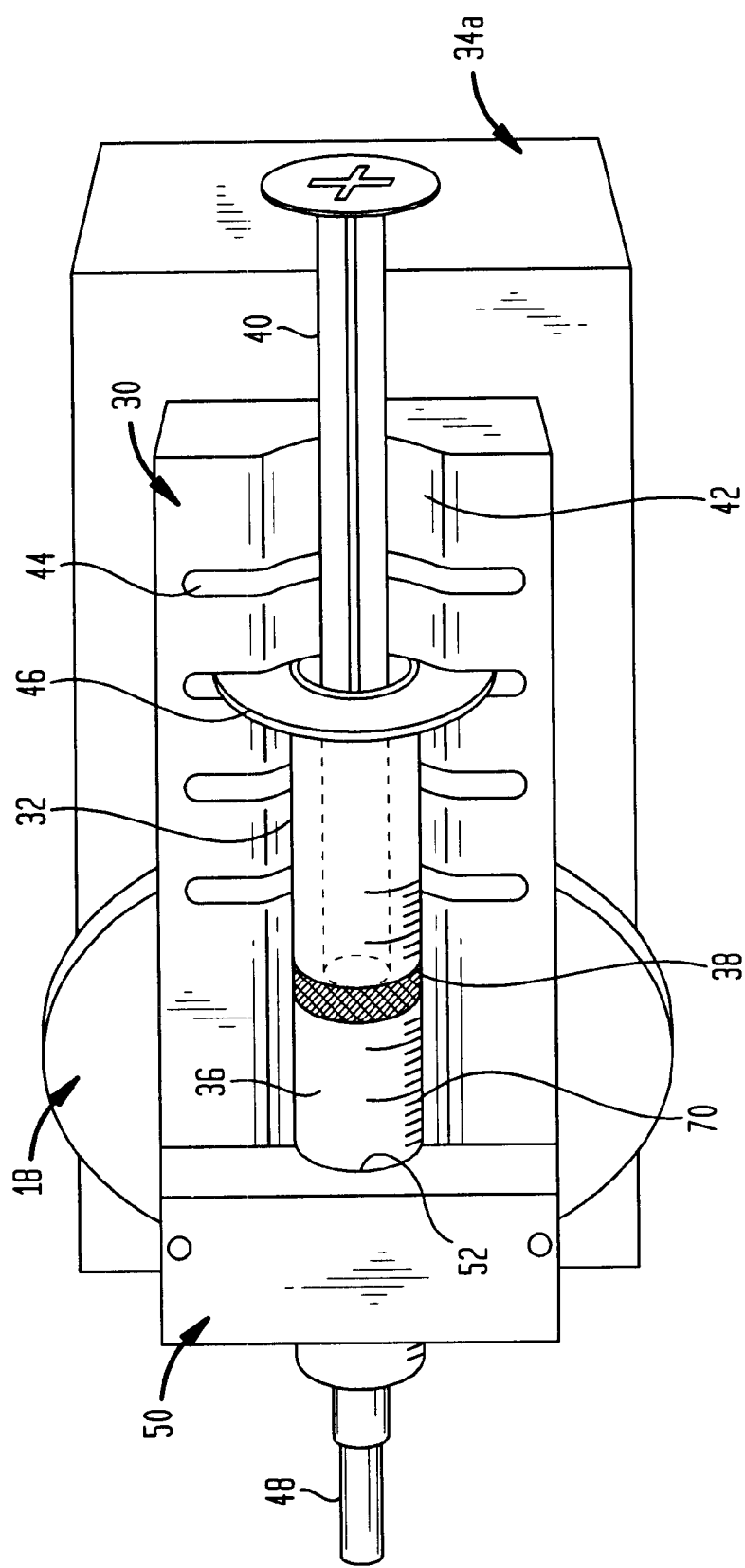

FIG. 2 shows holder 30 more clearly. The component 34a, on which the holder 30 is mounted in a linearly movable manner, is shown somewhat differently from the one according to FIG. 1. However, this is of no importance for the mode of operation.

Moreover, disk 18, which is eccentrically linked to the lower side of the holder 30, is seen. The syringe 32 is a conventional injection syringe with a syringe cylindrical barrel 36, a plunger 38 and a plunger rod 40. On the upper side, holder 30 has a channel 42, which is almost semicircular in its cross section, into which the syringe cylinder 36 is inserted. Transverse to channel 42 are grooves 44 which are formed at intervals and which accommodate a flange 46 at the end of cylinder 36. The dispensing end of syringe 32 is closed by means of a cap 48. A chuck or web-like component 50 has a channel-like recess 52, which accommodates a part of syringe cylinder 36, if it, as is shown in FIG. 2, is placed above syringe 32 in order to clamp same. The fastening of web 50 to holder 30 is carried out by means of screws or similar detachable fastening means.

A syringe like the syringe 32 is first filled outside of holder 30 and with plunger 38 removed with the two components that shall be mixed, e.g., a powdered bone cement component and a liquid component, one after the other. Subsequently, the plunger is pushed in under the load of sufficient clearance. Syringe 32, which has been closed by means of the cap 48, is then inserted into the holder 30 and fastened. The mixing movement can then be set in operation by applying a torque via the input transmission 22. A second container such as syringe 100 shown in FIG. 2A contains the liquid component which container may be supplied as part of a kit.

Figure 3:
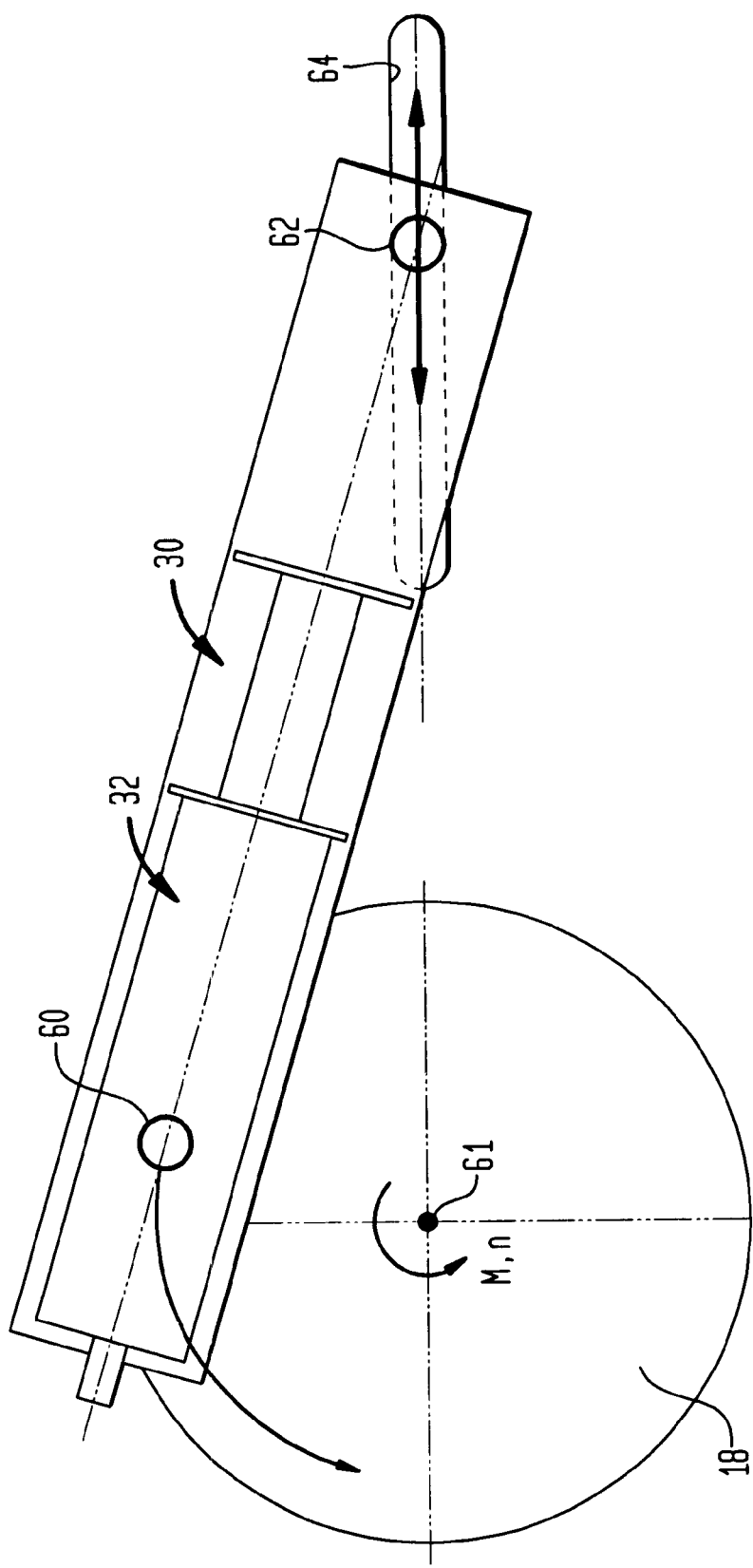
FIG. 3 schematically shows the structure for driving a holder of the mixing device according to FIGS. 1 and 2.

A structure, as is schematically shown in FIG. 3, is used for the mixing movement. Disk 18 is coupled via pin 60 to holder 30, which holder has a pin 62, which is guided linearly in an oblong slot 64 of the component 34a. With the rotation of disk 18 the syringe 32 with holder 30 performs a pivoting or eccentric movement around pin 62 with an amplitude, which is determined by the radius of the position of pin 60 from center of rotation 61. The amplitude also depends on the location of the syringe in the holder or the location of the holder on pin 60. At the same time, with a rotation of disk 18, pin 60 is moved back and forth in the longitudinal slot 64, whereby the stroke likewise depends on the radius of the position of pin 60.

After the mixing process which lasts, e.g., 30 seconds, the syringe 32 is removed from the holder 30 and fed into a dispensing device, which is able to accommodate the syringe with plunger. Thus, the front end of syringe 32 is manually accessible, so that the cap 48 can be removed and a hollow needle of a predetermined size can be placed thereon. The dispensing device which may be in the form of a typical caulking gun (not shown) has a feed bar, which cooperates with the plunger or the plunger rod 40 of the syringe 32. The feed bar, for its part, is actuated by a hand lever via a suitable transmission. The transmission may be selected so that the entire contents of the syringe 32 can be pressed out with a single stroke of the hand lever. However, it may also be designed so that several strokes of the hand lever are necessary. Since the syringe 32 has markings 70, it can be observed how much of the contents is dispensed with a stroke of the hand lever in each case.

The bringing together of the components and the holder of the syringe in the mixing device shall last less than one minute, if possible. With corresponding rotational speed of the disk 18, a mixing can be carried out within 30 seconds. The removal of the syringe, the insertion into a dispensing device and the processing shall not last longer than 5 minutes, if possible.

For the purpose of better handling, the device shown in FIGS. 1 and 2 can be detachably fastened to a background, e.g., a table top or a special stand.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A process for mixing and applying a flowable substance, which consists of a powdered first component and a liquid second component comprising:

placing the first component into a generally cylindrical barrel an injection syringe having a dispensing port and placing a closing means onto the dispensing port of the syringe;

placing the liquid second component in the injection syringe with the first component;

clamping the syringe barrel to a mixer using a moveable clamp having a part-cylindrical channel therein;

mixing the components by shaking the injection syringe; and removing the closing means of the injection syringe and placing a hollow needle onto the port of the injection syringe and delivering the flowable substance at a desired site.

2. The process for mixing as set forth in claim 1, wherein the liquid component is placed into the injection syringe through the dispensing port.

3. The process for mixing as set forth in claim 1, wherein the shaking is performed in an eccentric movement.

4. The process for mixing as set forth in claim 1, wherein the closing means is a cap.

5. A mixing device for a flowable substance consisting of a powdered first component and a liquid second component comprising:
   an injection syringe having a cylindrical barrel with a plunger and a removable closing means at a dispensing end as a mixing vessel for the first and second components;
   a holder for the detachable holding of said injection syringe, the holder including a moveable clamp having a cylindrical recess formed therein for engaging the syringe; and a mixing device which imparts on said holder a movement that arises from the superposition of a rotary and a translatory movement.

6. The device in accordance with claim 5, wherein an input transmission is arranged between said mixing device and an input shaft provided for inputting rotary motion to the input transmission, the input shaft mounted to a drive motor.

7. The device in accordance with claim 5 wherein said holder acts as a connecting rod of a connecting-rod device.

8. The device in accordance with claim 7, wherein an end area of said holder is eccentrically linked to a rotor, which is coupled with the output shaft of the input transmission, while the other end is mounted in a linearly movable manner.

9. The device in accordance with claim 5 wherein said closing means of said syringe is a cap.

10. The device in accordance with claim 5 wherein said holder has a mounting channel, which has, at intervals, transverse grooves for receiving a flange of said syringe cylinder.

11. A kit for mixing a bone cement made from powdered and liquid components comprising:
   at least one injection syringe having a powdered component stored therein and a dispensing port;
   at least one container having a liquid component stored therein; and
   a mixer having an eccentrically driven holder for receiving said injection syringe and imparting motion thereto having rotary and linear components, the holder including a moveable clamp having a cylindrical recess formed therein for engaging the syringe.

12. The kit as set forth in claim 11 further comprising at least one hollow needle for coupling to the dispensing port.

13. The kit as set forth in claim 11, wherein the powdered component is tetra-calcium phosphate and dicalcium phosphate.

14. The kit as set forth in claim 11, wherein the at least one container is a syringe.

15. The kit as set forth in claim 11 further including a rotary driver having an input shaft for driving said mixer.

16. The kit in accordance with claim 15, wherein an input transmission is arranged between said mixer and said input shaft provided for inputting rotary motion to the input transmission, the input shaft mounted to said driver, said transmission driving said mixer via an output shaft.

17. The kit in accordance with claim 16, wherein an end area of said holder is eccentrically linked to a rotor, which is coupled with the output shaft of the input transmission, while the other end is mounted in a linearly movable manner.

18. The kit in accordance with claim 11, wherein said dispensing part has a closing means in the form of a cap.

19. The kit in accordance with claim 11, wherein said holder has a mounting channel, which has, at intervals, transverse grooves for receiving a flange on a barrel of said injection syringe.

* * * * *

UNITED STATES PATENT AND TRADEMARK OFFICE
CERTIFICATE OF CORRECTION

PATENT NO.      : 6,626,912 B2
DATED           : September 30, 2003
INVENTOR(S)     : Andreas Werner Speitling It is certified that error appears in the above-identified patent and that said Letters Patent is hereby corrected as shown below:

<u>Title page,</u>
Item [57], ABSTRACT,
Line 4, "form" should read -- forms --.

<u>Column 2,</u>
Line 62, "embodiment" should read -- embodiments --.
Line 66, "2 A" should read -- 2A --.

<u>Column 4,</u>
Line 49, after "barrel" insert -- of --.

<u>Column 5,</u>
Line 2, after "component" (second occurrence) insert -- , especially bone cement, --.

Signed and Sealed this

Twenty-seventh Day of January, 2004

JON W. DUDAS
*Acting Director of the United States Patent and Trademark Office*